United States Patent [19]
Peterson et al.

[11] Patent Number: 5,782,791
[45] Date of Patent: Jul. 21, 1998

[54] METHOD OF MANUFACTURING A FLUID FILTER

[75] Inventors: Richard O. Peterson, Edina; Robert W. Olsen, Plymouth, both of Minn.

[73] Assignee: Avecor Cardiovascular, Inc., Plymouth, Minn.

[21] Appl. No.: 626,254

[22] Filed: Mar. 29, 1996

Related U.S. Application Data

[63] Continuation-in-part of Ser. No. 429,829, Apr. 27, 1995, Pat. No. 5,651,765.

[51] Int. Cl.⁶ .................. A61M 37/00; B01D 19/00
[52] U.S. Cl. .................. 604/4; 604/5; 210/188; 210/645; 210/493.1; 210/487; 210/436; 210/458; 210/472; 210/479; 156/210; 156/474
[58] Field of Search ............. 604/4–6; 156/73.6, 156/226, 227, 210, 474; 210/458, 436, 472, 477, 479, 480, 645–7, 315, 188, 497.01, 497.03, 321.86, 321.87, 493.1, 487, 512.1

[56] References Cited

U.S. PATENT DOCUMENTS

| | | |
|---|---|---|
| Re. 32,711 | 7/1988 | Dickens et al. . |
| D. 299,269 | 1/1989 | Pierson et al. . |
| 2,463,825 | 3/1949 | Strassheim . |
| 3,105,042 | 9/1963 | Roosa . |
| 3,306,794 | 2/1967 | Humbert, Jr. .......... 156/474 |
| 3,877,903 | 4/1975 | Peterson . |
| 4,113,627 | 9/1978 | Leason . |
| 4,149,288 | 4/1979 | Sendor et al. .......... 156/227 |
| 4,157,967 | 6/1979 | Meyst et al. . |
| 4,164,468 | 8/1979 | Raible . |
| 4,170,056 | 10/1979 | Meyst et al. . |
| 4,243,535 | 1/1981 | Behrends et al. . |
| 4,344,777 | 8/1982 | Siposs . |
| 4,430,223 | 2/1984 | Miyakawa et al. . |
| 4,493,717 | 1/1985 | Berger, Jr. et al. . |
| 4,622,132 | 11/1986 | Chupka . |
| 4,664,682 | 5/1987 | Monzen . |
| 4,744,902 | 5/1988 | Taki et al. . |
| 4,824,564 | 4/1989 | Edwards et al. . |
| 4,919,802 | 4/1990 | Katsura . |
| 4,932,987 | 6/1990 | Molina . |
| 4,964,984 | 10/1990 | Reeder et al. . |
| 5,114,508 | 5/1992 | Miyagi et al. .......... 156/227 |
| 5,127,900 | 7/1992 | Schickling et al. . |
| 5,258,127 | 11/1993 | Gsell et al. . |
| 5,302,301 | 4/1994 | Stamp et al. . |
| 5,312,479 | 5/1994 | Weinstein et al. . |
| 5,472,606 | 12/1995 | Steere et al. .......... 156/474 |

*Primary Examiner*—Robert A. Clarke
*Assistant Examiner*—Bruce E. Snow
*Attorney, Agent, or Firm*—Popovich & Wiles, P.A.

[57] ABSTRACT

A method of manufacturing a fluid filter comprising: (a) providing a cone having a tip end and an open end and made of a filter material; (b) providing a support element having a plurality of concentric annular members mounted on a base and having outermost and innermost concentric annular members; (c) aligning the central axes of the cone and the support element with the tip end of the cone closest to the support element; and (d) inserting a portion of the cone into a circular area between two concentric annular members by placing a forming sleeve inside the cone and inserting the forming sleeve between the two concentric annular members, the concentric annular members being generally cylindrical and having an interior and an exterior.

53 Claims, 10 Drawing Sheets

METHOD OF MANUFACTURING A FLUID FILTER

This application is a continuation-in-part of U.S. Ser. No. 08/429,829, filed Apr. 27, 1995, U.S. Pat. No. 5,651,765.

FIELD OF THE INVENTION

This invention relates to blood filters used in extracorporeal blood circuits. More particularly, the invention is directed to an arterial line blood filter used during heart bypass surgery to filter solid particulate and gaseous emboli from blood that has been oxygenated and is being returned to the patient. This invention also relates to a method of manufacturing a fluid filter, especially an arterial line blood filter.

BACKGROUND OF THE INVENTION

During open heart surgery the blood of the patient is bypassed to an extracorporeal blood circuit. The circuit commonly includes a support system which supplies the pumping function of the heart and the oxygenation function of the lungs. This support system effectively isolates the heart and lungs, enabling the surgeon to make the necessary repairs to the heart and/or lungs. Both venous blood and cardiotomy blood from the surgical site may be removed and circulated through the extracorporeal circuit.

Blood filters are typically included both upstream and downstream from the oxygenator, which may incorporate a heat exchanger. Upstream blood filters include venous and cardiotomy filters through which the blood may be filtered prior to entering the oxygenator and which are used to remove particulate, especially from the surgical site, and bubbles from the blood. Although these upstream filters are effective, it is possible that some emboli may pass through or be generated in the oxygenator and/or heat exchanger. These emboli may be in suspension in the oxygenated blood which is to be returned to the patient. The embolic material can be either particulate, such as platelet or white cell aggregates, or gaseous, such as small or large gas bubbles. Therefore, an arterial line filter which is located downstream of the oxygenator is critically important in trapping and removing any remaining emboli before the blood is provided to the patient.

Figure 1:
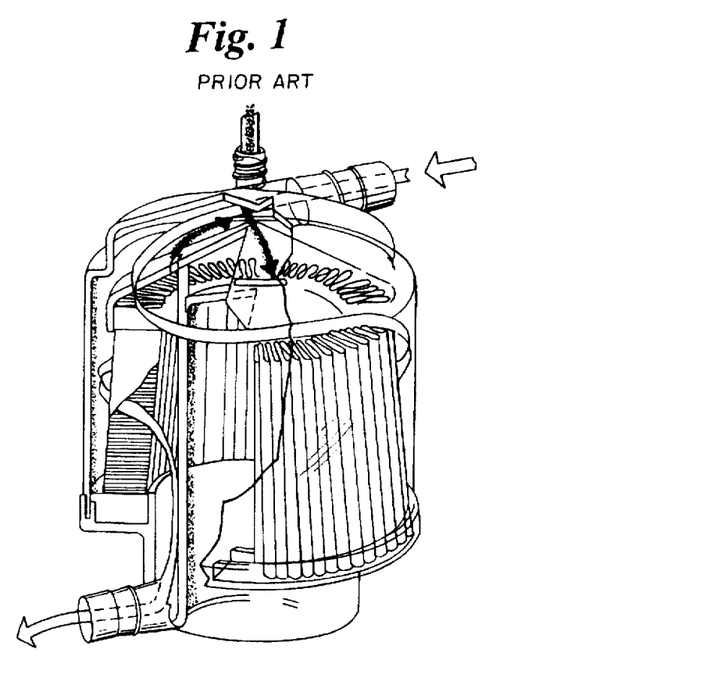
FIG. 1 is a partially cut away perspective view of a typical prior art arterial blood filter.

A typical conventional arterial blood filter is illustrated in FIG. 1. The filter includes a blood inlet located at the top of the filter. In this case the inlet is located in a tangential position. A radially pleated tubular filter is disposed within a cylindrical housing and is covered by a conically shaped cap. The arrow shows the path of blood as it flows through the filter. After entering through the tangential inlet the blood travels in a circular path over and around the cap and down between the outer wall of the housing and the pleated filter. The blood eventually passes through the filter and is discharged through a blood outlet at the bottom of the device. A gas port is located at the top of the is device through which air bubbles or gaseous emboli may be vented.

Although conventional arterial blood filters are effective in achieving significant reductions in emboli, they share several common problems. First, they include significant horizontal surface area in the blood flow path. Bubbles tend to attach themselves to these horizontal surfaces, increasing the difficulty of priming and, therefore, making the filters more difficult to use. Second, in many radially pleated designs, blood flows down through a small annular gap between the filter element and the housing. At a given flow rate, the smaller this area is, the higher is the downward blood velocity. Higher blood velocities entrain smaller air bubbles which subsequently get trapped in the filter element or get broken up into even smaller bubbles and pass through the filter. It would be desirable to have as large an area as possible available for downward flow to reduce downward entrainment of small air bubbles. Third, in many conventional arterial filters the priming volume is not utilized efficiently. Generally, the bigger the prime volume of a filter, the longer the time available for air bubbles to separate because of their buoyancy. However, there is also a desire to minimize prime volume to avoid unnecessary use of blood and blood products. The best balance is achieved by ensuring that as much of the prime volume as possible is upstream of the filter screen, because this is the region in which air can separate by buoyancy. Fourth, in most radially pleated designs the frontal area for flow downstream of the filter element is substantially reduced from the frontal area upstream of the filter element. Thus, the blood velocity significantly increases after it passes through the filter element in conventional designs. This higher velocity tends to entrain bubbles which have passed through the filter element and carries them toward the outlet port, where the bubbles may be conducted to the patient. It is desirable to maintain the frontal area for flow adjacent to the downstream side of the filter element as large as possible, or at least as close as feasible to the frontal area upstream of the filter element. Fifth, radially pleated designs incorporate a shallow annular or disk-shaped potting cup to mount the top and bottom of the filter element. The filter element end is immersed in the liquid potting compound and held in position until the compound solidifies. Since the cup is rarely completely filled with the potting compound, a concave surface is formed by the potting compound and the lip of the cup. Concave surfaces can also be created by the liquid potting compound wicking up the filter element while the compound is hardening from a liquid to a solid. In use, bubbles can become trapped under the concave surface of the upper potting cup. When the filter is inverted during priming to remove these trapped bubbles, they can rise and be trapped under the concave surface of the bottom potting cup which is now on top. This bubble trapping complicates priming the filter. It is desirable to create a design which does not require potting either the top or bottom of the filter element. Thus, it would be desirable to provide an arterial blood filter which not only has efficient emboli removal capabilities, but is also easier to prime and provides more opportunity for buoyancy separation of air than do conventional filters.

SUMMARY OF THE INVENTION

In accordance with the present invention there is disclosed a blood filter combining efficient filtering characteristics, large frontal area for flow, and a high prime volume upstream of the screen. The blood filter is easy to prime and overcomes the problems which exist in prior art devices. The blood filter is especially useful as an arterial blood filter. The blood filter comprises a housing having a cap portion, a base portion and a generally cylindrical wall portion. In one embodiment the inner surface of the cap defines an inwardly spiral blood flow path which slopes upward. A blood inlet is in flow communication with the inwardly spiral blood flow path. A filter element is disposed within the housing and divides the housing into an inlet chamber in flow communication with the blood inlet and an outlet chamber in flow communication with a blood outlet. The filter element may include a plurality of concentric annular pleats, the length of which may be substantially equal to the length of the wall portion between the cap portion and the base portion. The blood filter includes a support element having a base member and a plurality of concentric annular members nested within and supporting the annular pleats of the filter element. A gas vent is provided in gas flow communication with the inlet chamber.

The blood filter may include a volume displacing element disposed within an innermost annular pleat of the support element. The volume displacing element may be an extension of the cap portion. The annular members of the support element may be generally cylindrical and have an inner cylindrical surface, an outer cylindrical surface and an axis which coincides with the axis of the cylindrical wall portion. At least one of the inner cylindrical surface and the outer cylindrical surface of the annular members may be ribbed to provide spacing between the filter element and the support element. Further, each annular member may comprise a plurality of flat facets such that the annular members are in the shape of polyhedrons. The ends of the annular elements opposite the base member may be notched to allow more efficient blood flow.

In another embodiment, the invention provides a blood filter comprising a cap which defines an inwardly spiral blood flow path which slopes upward. The blood filter further includes a tubular wall section, and a base which, together with the cap, define a blood filtering chamber. A blood inlet is provided in flow communication with the inwardly spiral blood flow path. A filter element disposed within the housing divides the housing into an inlet chamber in flow communication with the blood inlet and an outlet chamber in flow communication with a blood outlet. The filter element is provided with a plurality of concentric annular pleats, each pleat having a length equal to approximately the length of the tubular wall section. A volume displacing element integral with the cap extends towards the filter element such that it is disposed within an innermost annular pleat of the filter element. A support element having a base member and a plurality of concentric annular members extends from the base member and terminates at an edge which nests within and supports the annular pleats of the filter element. The blood filter has a gas vent in flow communication with the inlet chamber.

The annular members of the support element may be generally cylindrical and have an inner cylindrical surface, an outer cylindrical surface and an axis which coincides with the axis of the cylindrical wall portion. At least one of the inner cylindrical surface and the outer cylindrical surface of the annular members are ribbed to provide spacing between the filter element and the support element. Each annular member may comprise a plurality of flat facets such that the annular members are in the shape of polyhedrons. The supporting edges of the annular elements may be notched to provide more efficient blood flow.

In a further embodiment the invention comprises a method for filtering blood. The method comprises providing a blood filter having a housing which defines a blood filtering chamber. The chamber is divided into a blood inlet chamber and a blood outlet chamber by a filter element. In one aspect of the invention the filter element may include concentric pleats. The concentric pleats are supported in the chamber by a support element having a plurality of concentric annular members nested in the concentric pleats of the filter element. The method includes circulating blood through a blood inlet into the inlet chamber. The blood flow may be directed in an inwardly spiral and upward blood flow path such that the blood is distributed over and flows through the concentric annular pleats of the filter element. Particles and bubbles are filtered from the blood as it passes through the filter element to the outlet chamber. The blood is discharged from the outlet chamber through a blood outlet. The method may further include removing air from the inlet chamber through a vent provided at a top portion of the inlet chamber.

In another embodiment the invention comprises a method of manufacturing a fluid filter. The method comprises providing a cone having a tip end and an open end and made of a filter material and providing a support element having a plurality of concentric annular members mounted on a base and having outermost and innermost concentric annular members. The central axes of the cone and the support element then are aligned with the tip end of the cone closest to the support element. Next, a portion of the cone is inserted into a circular area between two concentric annular members by placing a forming sleeve inside the cone and inserting the forming sleeve between the two concentric annular members. The concentric annular members are generally cylindrical and have an interior and an exterior.

BRIEF DESCRIPTION OF THE DRAWINGS

The foregoing and other aspects of the present invention will be best appreciated with reference to the detailed description of the invention, which follows, when read in conjunction with the accompanying drawings wherein.

DETAILED DESCRIPTION OF THE INVENTION

Figure 2:
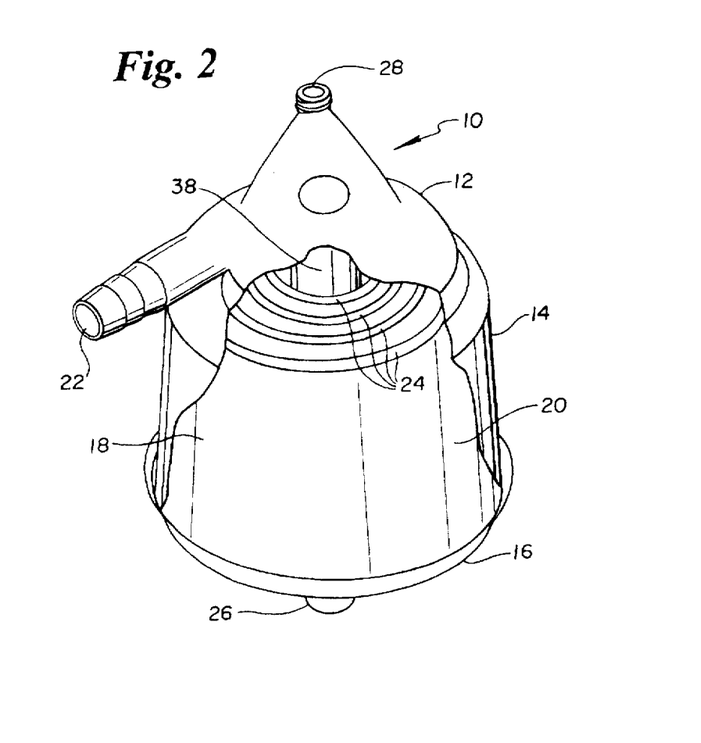
FIG. 2 is a perspective view of an arterial blood filter according to the present invention with a portion of the housing broken away to show the concentric pleats of the filter element.
Figure 3:
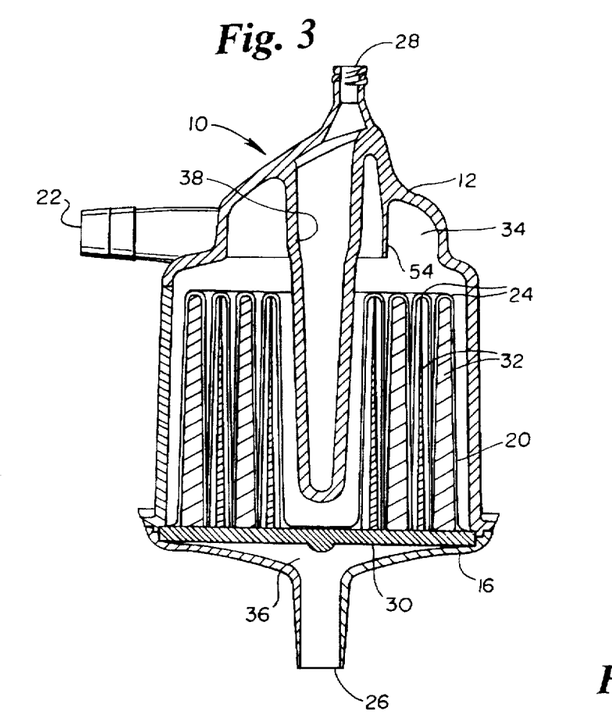
FIG. 3 is a cross-sectional side view of the arterial blood filter of FIG. 2.

Construction of the Blood Filter FIGS. 2 and 3 are perspective and sectional views of an arterial blood filter 10 in accordance with the present invention. Blood filter 10 has a housing which includes a cap portion 12, a tubular wall portion 14 and a base portion 16. The housing encloses a blood filtering chamber 18 which contains a filter element 20 having a plurality of concentric pleats 24. As will be discussed in more detail with respect to FIGS. 3 and 6 to 8, filter element 20 is supported by a support element, not shown in FIG. 2. Cap portion 12, wall portion 14 and base portion 16 may be formed from separate pieces and bonded together in a conventional manner. Alternatively, wall portion 14 may be constructed as an integral piece with either cap 12 or base portion 16. In the preferred embodiment shown in FIGS. 2 and 3 the cap portion 12 is integral with wall portion 14. Preferably, the housing is made of a transparent medical grade material so that the user is able to observe the flow of blood through the device.

A blood inlet 22 is located at an upper position on the housing to enable blood to be circulated through the blood filtering chamber 18. Blood inlet 22 may be connected to a line from an oxygenator (not shown) for receiving oxygenated blood. In the embodiment shown in FIG. 2 the blood inlet is formed as an integral portion of cap 12. Inlet 22 is constructed such that when the filter is placed in its upright position with the cap at the top, as shown in FIG. 2, the blood enters horizontally at one side of the blood filter. After the blood enters the blood filter it is directed by the cap in an inwardly spiral path, as will be discussed in more detail with respect to FIGS. 4 and 5. A blood outlet 26 is located at the bottom of the housing in the base portion 16. The outlet 26 is connected to a patient return line (not shown) for providing oxygenated blood back to the patient. A gas vent 28 is located at or near the top of cap portion 12. Vent 28 provides a means of venting from the blood filter gaseous emboli which rise to the top of cap portion 12. The vent 28 is located at the highest point of cap 12.

FIG. 3 is a cross-sectional side view of the arterial blood filter of FIG. 2. A support element 30 is positioned within the housing to provide support for the concentric pleats 24 of filter element 20. Generally, any manner of support which results in stabilizing the annular pleats may be used. Preferably, support element 30 includes a plurality of concentric annular members 32, each larger in diameter than the previous, which nest within the concentric pleats 24. Each annular member is a generally cylindrical tubular section. As shown in FIG. 3, the pleats are generally concentric to the longitudinal axis of the blood filter and spaced apart from the surrounding wall portion and each other to leave sufficient space for blood to flow down and through the filter member. Inside of the innermost concentric pleat is a volume displacer 38. Volume displacer 38 is a closed end tube which extends from the cap portion 12 towards the base portion 16. It may be formed as an integral part of cap portion 12, as shown, or it may be a separate piece which is bonded to the cap portion. Although volume displacer 38 is optional, its use is desirable since it serves the important function of lowering the priming volume of the blood filter.

The Concentric Pleated Filter Element

The concentric pleats of the filter element are formed from a conventional filter screen fabric. The filter screen fabric is cut and one or more seams bonded so the resulting shape is a hollow cone. The axis of the pattern may be cut on the bias of the screen threads. A bias cut allows the screen to conform better to the desired shape without forming wrinkles, creases, or bulges. The cone may be formed into concentric pleats by shaping the screen over the annular members of the support element using cylindrical forming sleeves.

The filter element 20 is bonded along the outer periphery of the support element 30. The filter screen is also bonded to each spoke of the filter support element to prevent the screen cone from inverting if flow through the filter is retrograde. Support element 30 is in turn bonded to the base portion 16 such that when the blood filter is assembled, filter element 20 divides blood filtering chamber 18 into a blood inlet chamber 34 and a blood outlet chamber 36.

With continued reference to FIG. 3, it will be appreciated that the length of the annular members 32 of the support element 30 is approximately the same as the length of the wall portion 14 between the cap portion 12 and the base portion 16. Thus, the pleated filter element formed over the support element approximately fills the blood filtering chamber between the cap portion and base portion of the housing. This configuration is desirable in order to maximize the amount of surface area of the filter element which is exposed to blood flow. Additionally, the support element 30 and its annular members 32 provide the added benefit of displacing additional volume, resulting in the further lowering of the priming volume of the blood filter on the downstream side of the filter screen.

The number of annular pleats (and consequently the number of annular members) is selected to maximize the surface area of the filter element which is exposed to blood flow while at the same time leaving enough space between adjacent pleats, the wall portion and the volume displacer so that efficient blood flow may be maintained. In the preferred embodiment shown, four pleats are used. However, it will be appreciated by those of skill in the art with knowledge of the present invention that fewer or more pleats may be used within the scope of the invention.

The Support Element

Figure 6:
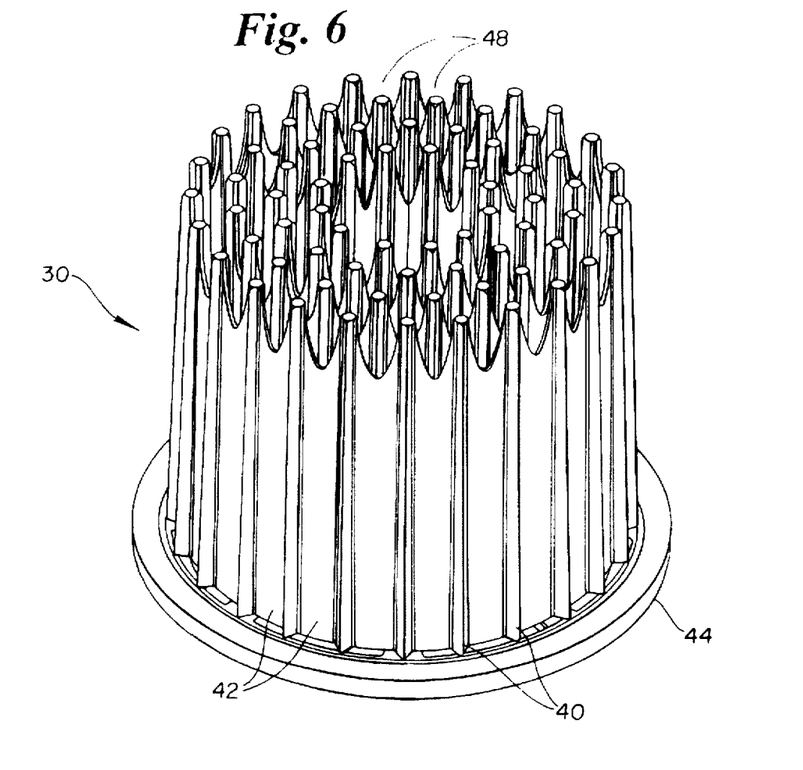
FIG. 6 is a perspective view of the support element utilized in the arterial blood filter of FIG. 2.
Figure 7:
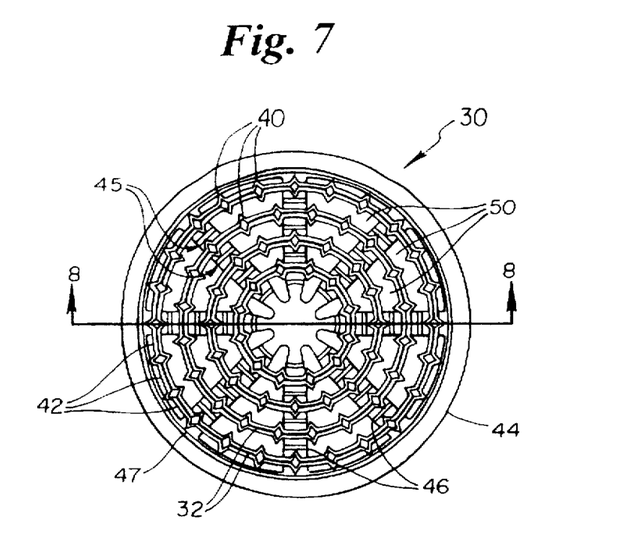
FIG. 7 is a top view of the support element of FIG. 6.
Figure 8:
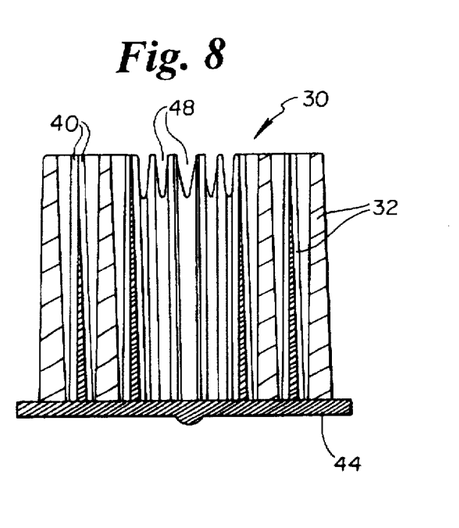
FIG. 8 is a sectional view of the support element taken along line 8—8 of FIG. 7.

Support element 30 is shown in more detail in FIGS. 6 to 8. FIG. 6 is a perspective view of the support element showing the concentric ringed configuration of the annular members. FIG. 7 is a top view of the support element. FIG. 8 is a cross-sectional view of the support element taken along line 8—8 of FIG. 7. Support element 30 includes a base ring 44. Base ring 44 provides support for a network of spokes 46 from which the annular members 32 project. Each of the components including base ring 44, spokes 46 and annular members 32 may be made separately and then bonded together in a conventional manner to form support element 30. Preferably, support element 30 is molded from a medical grade plastic as a single integral piece which is bonded in a conventional manner to base portion 16. Alternatively, support element 30 may be formed as an integral portion of base portion 16.

In order to hold the filter element off of the surface of the annular members, ribs 40 may be provided on the inner and/or outer cylindrical surfaces of one or more of the annular members. In the preferred embodiment shown in the figures, the ribs are diamond shaped in cross-section, are generally parallel to the longitudinal axis of the blood filter and protrude from both the inner and outer cylindrical surfaces of each annular member. The number of ribs and their orientation with respect to the surface of the annular members may be varied. For example, the ribs may project from either the inner cylindrical surface or the outer cylindrical surface or both, as shown. Likewise, the ribs need not be parallel to the axis of the blood filter. Preferably, the ribs on the outer surface of one cylindrical annular member do not line up with the ribs on the inner surface of the adjacent annular member. This facilitates the molding process since it allows the metal in the mold to be thicker at the base of the support element where the ribs are in closest proximity. This enables the mold to be made stronger and more durable. It also conducts heat more rapidly so it cools more quickly after the plastic is injected during the molding process. The ribs provide a path between the filter element and the cylindrical surface of the annular members for blood which has passed through the filter element to flow from the outlet chamber to the blood outlet.

The cylinders which form the annular members may comprise flat planar facets 42 between ribs 40 such that the resultant shape is a polyhedron. Such a configuration maximizes the gap between the filter element and the inner and outer surfaces of the facets. This further ensures that the blood flow path between the filter element and the surfaces of the facets is adequate. In order to minimize the surface area of the filter element which is blocked off by contact with the upper edge of the annular members, the top edge of the facets 42 may be provided with notches 48. Notches 48 allow blood to flow through the filter element at the top of the pleats in areas that would be blocked in the absence of the notches. After passing through the filter element, the blood flows in a downward direction through outlet slots 50 formed between spokes 46 and annular members 32 and out of the blood filter through blood outlet 26.

Inlet Blood Flow Path

Figures 4, 5:
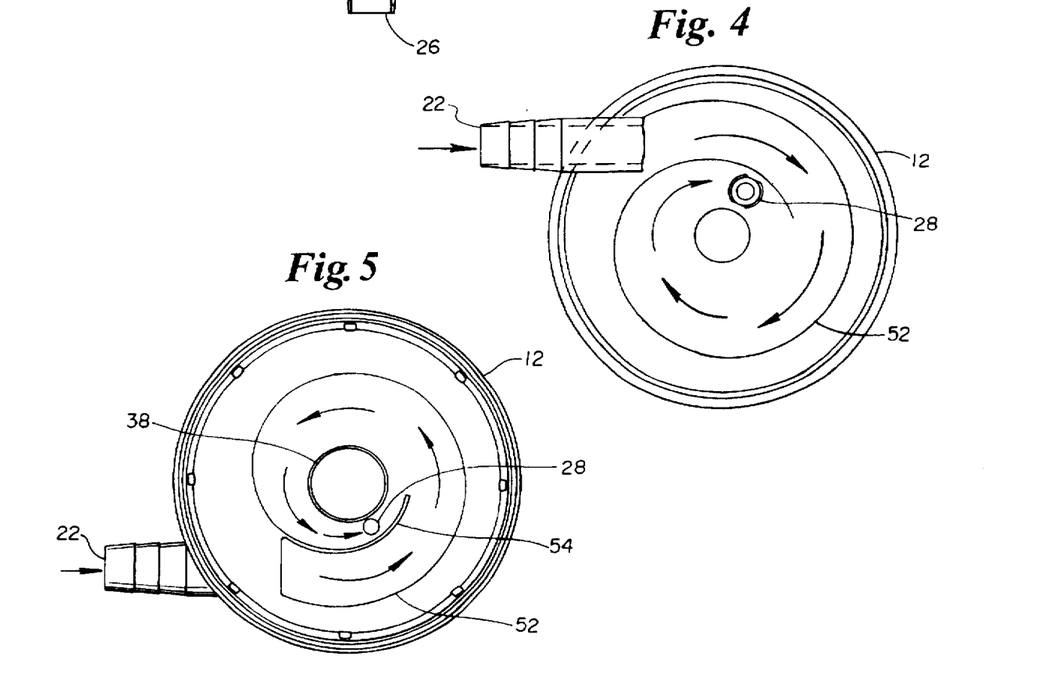
FIG. 4 is a top view of the cap of the arterial blood filter of FIG. 2.
FIG. 5 is a bottom view of the cap of FIG. 4.

The path followed by blood from the inlet 22 is best shown in FIGS. 4 and 5. FIGS. 4 and 5 are top and bottom views of cap portion 12, respectively. As illustrated by the arrows, the blood is directed to flow in an inward spiral by the inner surface 52 of cap portion 12. The tightness of the spiral increases along the flow path as the blood is directed around the volume displacer 38 inwardly towards the center of the blood filter. A flow director 54 is provided to separate blood which has circled around the blood filter from blood just entering through the blood inlet. Such interaction could reduce the cross sectional area available for flow of the inlet blood. This would increase the blood velocity in this region, which can increase the pressure losses in the inlet, increase damage to the blood and disrupt the even supply of blood over the pleats of the filter element. In addition, the flow director prevents bubbles which are rising to the vent port from mixing with blood entering from the inlet which is traveling at a high velocity. This prevents the high velocity inlet blood flow from breaking up bubbles rising to the vent port and from entraining those bubbles.

Operation of the Blood Filter

In use, blood enters the inlet chamber through blood inlet 22. The blood flow is directed by the shape of inner surface 52 of the cap portion 12 in an inward spiral. Since the cross-sectional flow area in the inlet chamber is greater than the cross-sectional area of the inlet tubing, the inlet chamber acts as a diffuser and decreases the velocity of the blood. As the blood continues its flow at a decreased velocity around the cap portion of the blood filter, some blood begins to flow downward into the concentric annular pleats. Because the blood velocity is decreased and the blood is directed inwardly, there tends to be an even distribution of blood over the pleats.

As the blood follows its path through the filter, gaseous emboli rise to the top surface of the cap portion which is sloped upward and toward the vent. The inward flow path of blood carries the emboli around the spiral to the elevated region of the vent where they collect for venting. The elevated region of the vent is above the blood flow path so that the area is protected from high velocity blood flows which would flush the gaseous emboli out of the elevated vent region.

As the blood is distributed over the concentric pleats it passes through the filter element into the output chamber. The blood is then directed by the cylindrical annular members downward and through the output slots. From there it exits the blood filter through the blood outlet where it may be delivered to a patient through a patient return line.

Method of Manufacturing a Fluid Filter

A method of manufacturing a fluid filter is described below. The method of manufacturing is especially useful for manufacturing a blood filter.

The invention provides a method of manufacturing a fluid filter comprising: (a) providing a cone having a tip end and an open end and made of a filter material; (b) providing a support element having a plurality of concentric annular members mounted on a base and having outermost and innermost concentric annular members; (c) aligning the central axes of the cone and the support element with the tip end of the cone closest to the support element; and (d) inserting a portion of the cone into a circular area between two concentric annular members by placing a forming sleeve inside the cone and inserting the forming sleeve between the two concentric annular members. The concentric annular members are generally cylindrical and have an interior and an exterior.

In a preferred embodiment, the forming sleeve is an annular forming sleeve. Other types of forming sleeves such as those having a plurality of prongs that may be inserted into the support element may also be used. In one embodiment, a second portion of the cone is inserted into the circular area in the interior of the innermost annular member by a forming sleeve; in another embodiment, a second portion of the cone is formed over the exterior of the outermost annular member by a forming sleeve inserted outside the outermost annular member. In a preferred embodiment, a second portion of the cone is inserted into the area in the interior of the innermost annular member and a third portion of the cone is formed over the exterior of the outermost annular member by inserting a forming sleeve outside the outermost annular member.

In an embodiment of the invention, the portions of the cone inserted into the support element are inserted substantially all of the distance to the base of the support element. In a preferred embodiment, each portion of the cone which is inserted into the support element is inserted all of the distance to the base of the support element.

In another embodiment, each of a plurality of portions of the cone is inserted into separate circular areas between two concentric annular members by a plurality of forming sleeves. In a preferred embodiment, the portions of the cone that are inserted into the support element are inserted in order from the innermost to outermost circular areas.

In another embodiment of the invention, one or more of the portions of the cone which are inserted into the support element are attached to the base of the support element. However, it is not necessary to attach the cone to the base of the support element; the filter performs well even if the cone is just pleated over the support element. The portions of the cone may be attached to the base of the support element by ultrasonic vibrations (ultrasonic staking), by inserting a portion of the cone into a groove on the base of the support element, or by an adhesive. In a preferred embodiment, the portions of the cone that are inserted into the support element are attached by inserting a portion of the cone into a groove on the base of the support element, and then subjecting the base of the support element to ultrasonic vibrations. In a preferred embodiment, the ultrasonic vibrations are conducted through energy directors. In another preferred embodiment, the support element has a lower melting temperature than the cone.

The cone also may be attached to the base of the support element by one or more additional support elements placed on top of the cone and support element. The one or more additional support elements may be placed outside the outermost member, or inside the concentric annular members. These one or more additional support elements preferably interlock with the support element.

In one embodiment, the base of the support element is cylindrical. In preferred embodiments of the invention, the support element has from two to six concentric annular members, more preferably from two to four concentric annular members. In another embodiment, the support element has four concentric annular members.

The forming sleeves may be inserted into the support element by an automated machine. A preferred automated machine comprises a base and retractable forming sleeves. Using this machine, the open end of the cone is placed partially over the base of the automated machine with the forming sleeves retracted and then the forming sleeves are extended. The support element then is moved toward the cone after the sleeves are extended, and the support element is brought in contact with each forming sleeve in succession until the cone is pleated. Alternatively, the support element may be fixed and the cone and the extended forming sleeves moved toward the support element. Each forming sleeve is then brought into contact in succession with the support element until the cone is pleated.

The invention also provides an alternate method of manufacturing a fluid filter in which the central axes of the cone and the support element are aligned with the open end of the cone closest to the support element. A portion of the cone is inserted into a circular area between two concentric annular members by placing a forming sleeve over the cone and inserting the forming sleeve between the two concentric annular members.

The invention also provides a method of manufacturing a fluid filter comprising: (a) providing an unassembled housing having an integrated cap portion and a generally cylindrical wall portion and a separate base portion; (b) dispensing adhesive into the separate base portion; (c) inserting the support element containing a portion of the cone into the separate base portion and into the adhesive; and (d) attaching the integrated cap portion and generally cylindrical wall portion to the separate base portion. In a preferred embodiment the fluid filter is a blood filter, the integrated cap portion and a generally cylindrical wall portion comprises a blood inlet and a gas vent, and the separate base portion comprises a blood outlet. The adhesive is preferably cured by ultraviolet radiation.

The invention also provides another method of manufacturing a fluid filter comprising: (a) providing an unassembled housing having an integrated cap portion and a generally cylindrical wall portion and a separate base portion; (b) dispensing adhesive into the separate base portion; (c) inserting a filter element into the separate base portion and into the adhesive; and (d) attaching the integrated cap portion and generally cylindrical wall portion to the separate base portion so that the adhesive is disposed between the integrated cap portion and generally cylindrical wall portion and the separate base portion, between the integrated cap portion and generally cylindrical wall portion and the filter element, and between the separate base portion and the filter element. In a preferred embodiment the fluid filter is a blood filter. In another preferred embodiment, the fluid filter is a blood filter, the integrated cap portion and a generally cylindrical wall portion comprises a blood inlet and a gas vent, and the separate base portion comprises a blood outlet. The adhesive is preferably cured by ultraviolet radiation. In a preferred embodiment, the filter element is produced as described above and a portion of the cone is disposed in the adhesive. In another preferred embodiment, the filter element is produced as described above, a first additional portion of the cone is formed over the exterior of the outermost annular member by a forming sleeve inserted outside the outermost annular member, and the first additional portion of the cone is attached within the fluid filter by the adhesive. In another embodiment, the filter element is produced as described above, a first additional portion of the cone is formed over the exterior of the outermost annular member by a forming sleeve inserted outside the outermost annular member, and the first additional portion of the cone is attached within the fluid filter by inserting it within the joint between the integrated cap portion and generally cylindrical wall portion and the separate base portion.

A specific embodiment of the method of manufacturing a fluid filter is described below in the context of a blood filter. The manufacturing process for the blood filter comprises the following steps: (1) assembly of the filter cone 60, (2) pleating the filter cone 60 onto the support element 30, (3) ultrasonically staking (attaching) the filter cone 60 to the support element 30, (4) trimming the pleated cone 60, (5) dispensing the ultraviolet radiation (UV) activatable adhesive into the base portion 16, (6) placing the support element 30 on top of the adhesive, (7) lowering the integrated wall portion 14 and cap portion 12 onto the separate base portion 16 until it locks into the snap joint 17, and (8) curing the UV activatable adhesive.

1. Assembly of the Filter Cone 60

The filter screen fabric is cut to size and is seam-bonded so the resulting shape is a hollow three-dimensional cone with a rounded tip. The cone can be fabricated from either one or two pieces of filter screen. The axis of the cone pattern is preferably cut on the bias of the screen threads. This bias cut allows the screen to conform to the shape of the support element without forming wrinkles, creases, or bulges.

Figure 9:
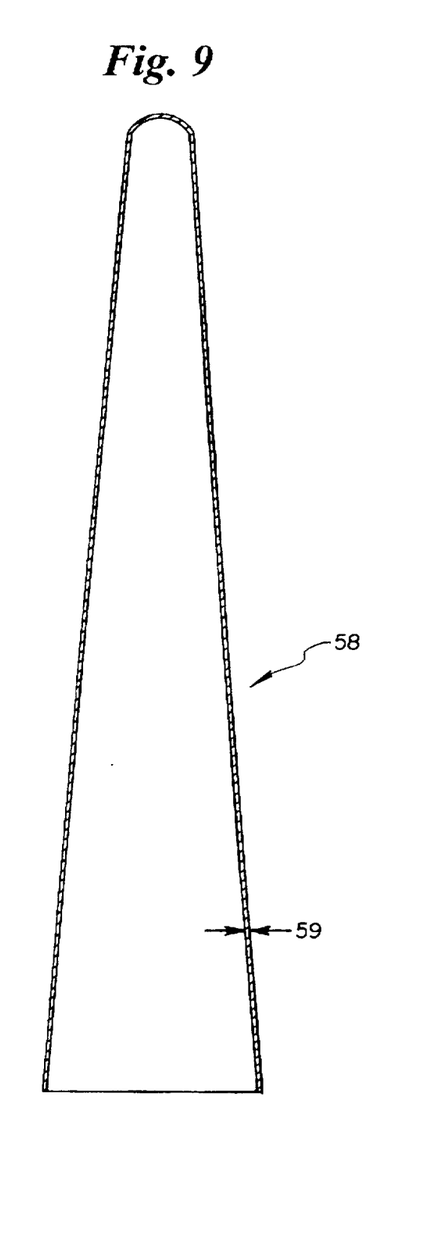
FIG. 9 is a front view of a flat pattern for a filter cone.

A single piece cone may be made from a two-dimensional flat pattern which has the shape of a two-dimensional cone with an arc for the base. The flat piece may be wrapped around a solid three-dimensional cone to form the correct shape and the single seam may be bonded. In a preferred method, the filter screen cone 60 is made from two pieces. The flat pattern 58 for a two piece cone is shown in FIG. 9. The second piece is laid on top of the first piece and the side and tip seams are bonded. Note that the seam 59 is on the outside of the cone with either of these methods of fabrication.

The seams of the filter cone 60 may be bonded by one of several processes. Adhesive strips or sheets may be placed between the two pieces, below the bottom piece, above the top pieces, or a combination of the above. The adhesive is activated (melted) by an energy source such as UV, ultrasonic vibrations, or an impulse heater, and the adhesive is caused to flow such that it contacts both the upper and lower pieces of the cone. The energy source is turned off and the adhesive is allowed to solidify and bond the two pieces of filter screen together. The two pieces could also be bonded with a contact adhesive or fused together without an adhesive by using an energy source to melt the two pieces of filter screen together. For a polyester screen, the preferred energy source is ultrasonic vibrations.

2. Pleating the Filter Cone 60 Onto the Support Element 30

As noted above, the filter cone 60 may be pleated manually using a series of concentric cylindrical forming sleeves 80. In a preferred embodiment, the filter cone 60 is pleated by an automated machine.

Figure 10:
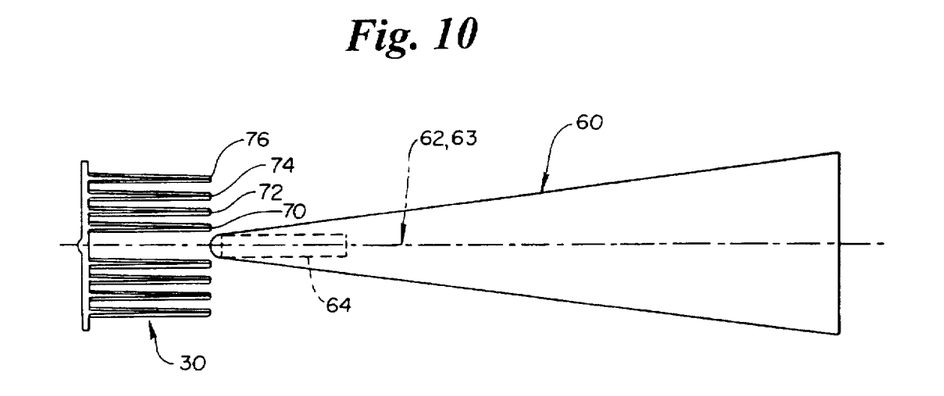
FIGS. 10 to 14 are cross-sectional side views of steps in the manual pleating of the filter cone, with the pleats formed inside pleat first.

The filter cone 60 may be manually formed into concentric pleats by shaping the filter cone 60 over the cylindrical support element 30 using cylindrical forming sleeves 80. The support element 30 has a series of concentric annular members 70, 72, 74, and 76, each larger in diameter than the previous one (see FIGS. 6, 7, and 10). Forming sleeves 66, 67, and 68 are sized to fit between the annular members 32 of the support element 30. The first forming sleeve 64 fits inside the first annular member 70 of the support element 30 and the fifth sleeve 69 fits outside the fourth annular member 76 of the element 30. The filter cone 60 may be pleated inside pleat first or outside pleat first.

Figure 11:
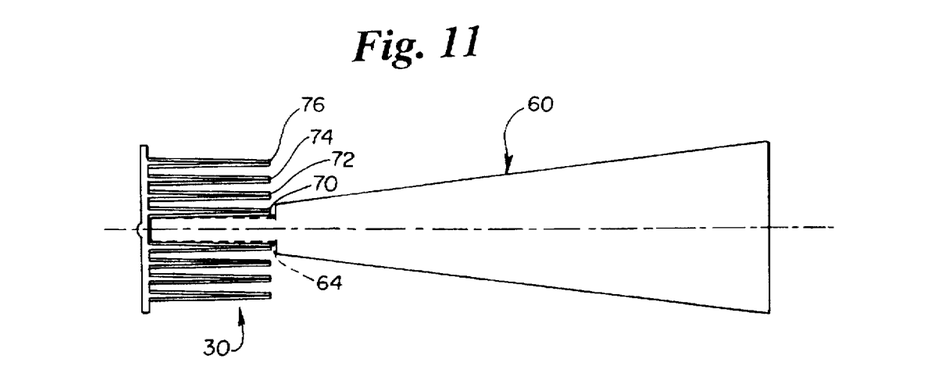
Figure 12:
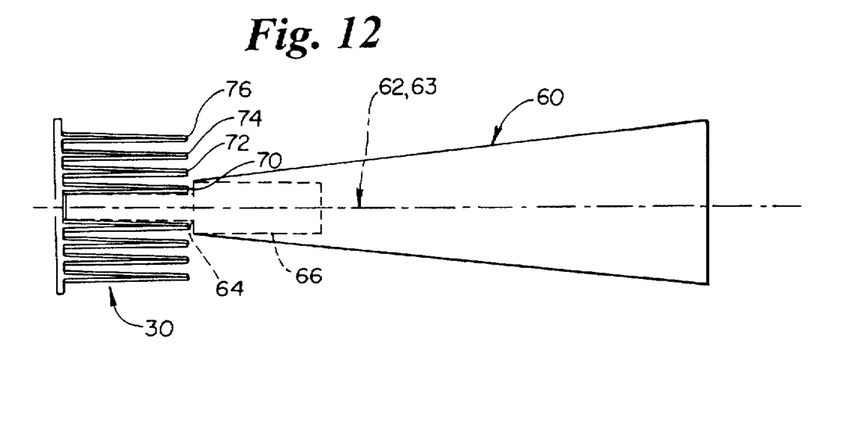
Figure 13:
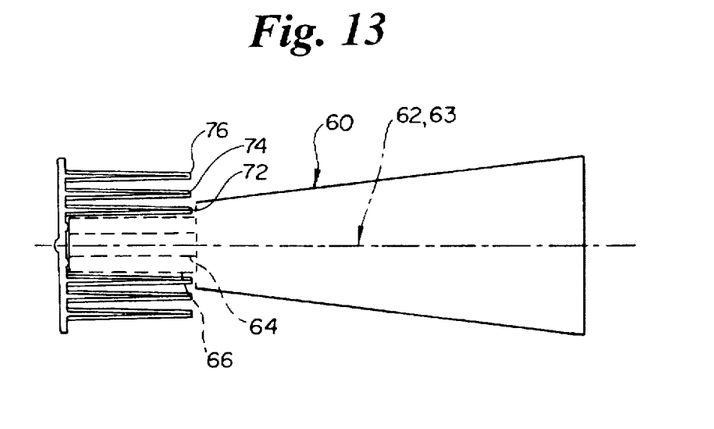
Figure 14:
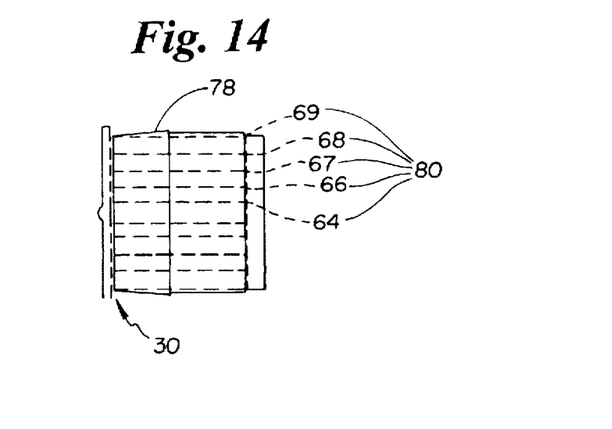

To pleat the filter cone 60 inside pleat first, the following procedure may be used. With the central axis 62 of the cone 60 aligned along the central axis 63 of the support element 30, the tip of the cone 60 is placed toward the support element 30 with the open end of the cone 60 away from the element 30. The first (smallest) forming sleeve 64 is inserted inside the cone 60 (FIG. 10) and used to drive the tip of the cone 60 down into the first (inner) annular 20 member 70 and into the grooves 45 on the surface of the spokes 46 of the support element 30 (FIG. 11). With the first sleeve 64 remaining in place, the next largest sleeve is inserted into the cone 60 (FIG. 12) and used to drive the cone 60 into the space between the annular members 70 and 72 and into the grooves 45 on the spokes 46 (FIG. 13). Note that this process inverts the cone from its orientation of fabrication and places the seam on the inside surface of the pleats, which is desirable because the seam is on the outlet side of the filter screen 60. The seam holds the screen away from the annular members much as the vertical ribs on the annular members perform this function. The cosmetic appearance of the pleats also is improved by having the seam on the outlet side of the filter screen. This process may be performed at either a vertical, horizontal, or sloped orientation as long as the central axes of the filter cone 60 and support element 30 are aligned. The process is continued until the fifth (largest) sleeve 69 is used to pleat the cone 60 over the outside of the support element 30 and into circular groove 47 (FIG. 14). Some extra cone material 78 will extend away from the support element 30 on the outside of the fifth forming sleeve 69.

Figure 15:
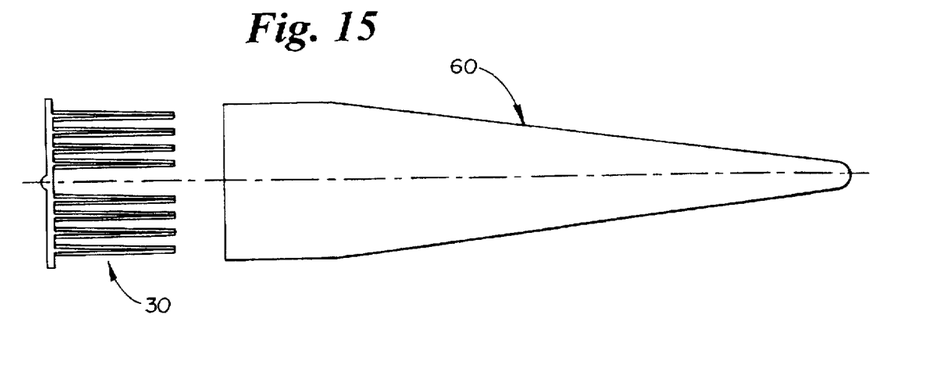
FIGS. 15 to 17 are cross-sectional side views of steps in the manual pleating of the filter cone, with the pleats formed outside pleat first.
Figure 16:
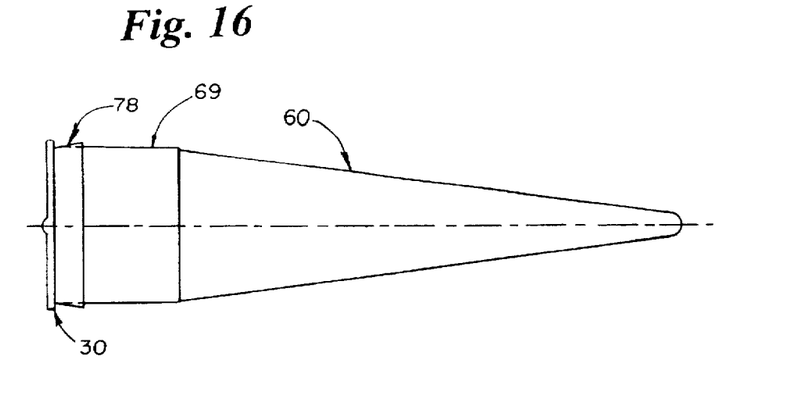
Figure 17:
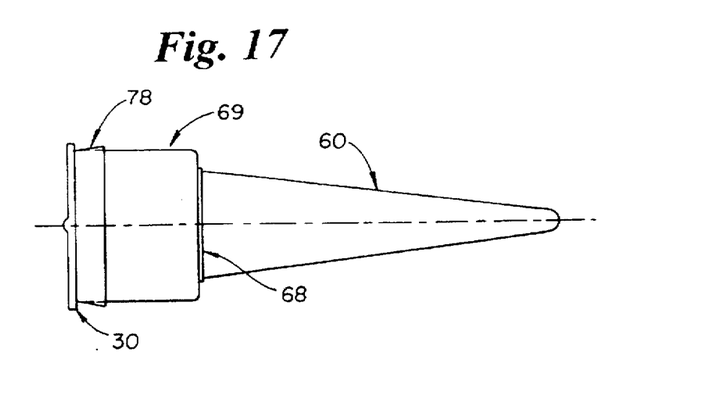

To pleat the filter cone 60 outside pleat first, the following procedure may be used. With the central axis 62 of the cone 60 aligned along the central axis 63 of the support element 30, the open end of the cone 60 is placed toward the support element 30 with the tip of the cone 60 away from the element 30 (FIG. 15). The fifth (largest) sleeve 69 is slipped over the outside of the cone 60 and is used to drive the cone 60 onto the outside of annular member 76 and into circular groove 47 (FIG. 16). With the fifth sleeve 69 remaining in place, the fourth (next largest) sleeve 68 is slipped over the cone 30 and used to drive the cone 30 into the space between annular members 76 and 74 and into the grooves 45 on the surface of the spokes 46 of the support element 30 (FIG. 17). Note that this method does not invert the cone. This process may be performed at either a vertical, horizontal, or sloped orientation as long as the central axes of the filter cone 60 and support element 30 are aligned. The process is continued until the first (smallest) sleeve 64 is used to form the inner pleat.

Figure 18:
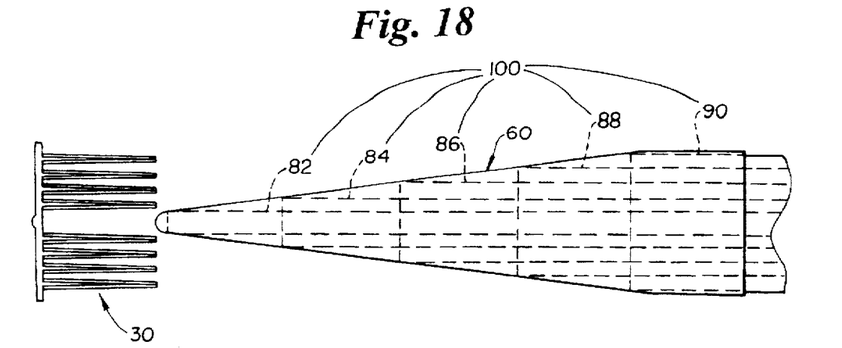
FIGS. 18 to 23 are cross-sectional side views of steps in the automated pleating of the filter cone.
Figure 19:
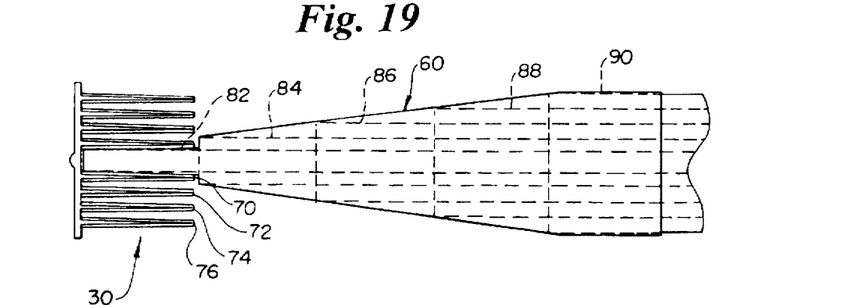
Figure 20:
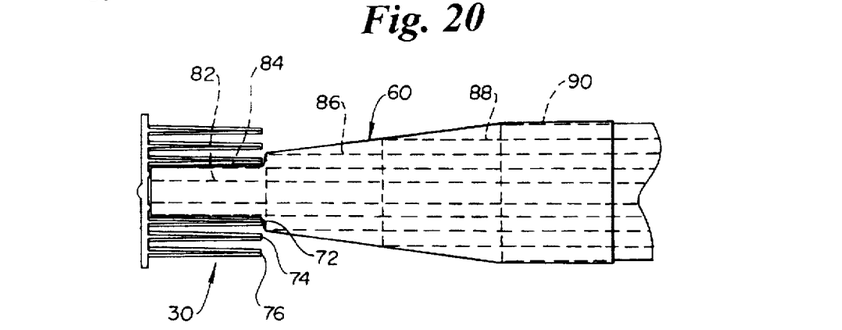
Figure 21:
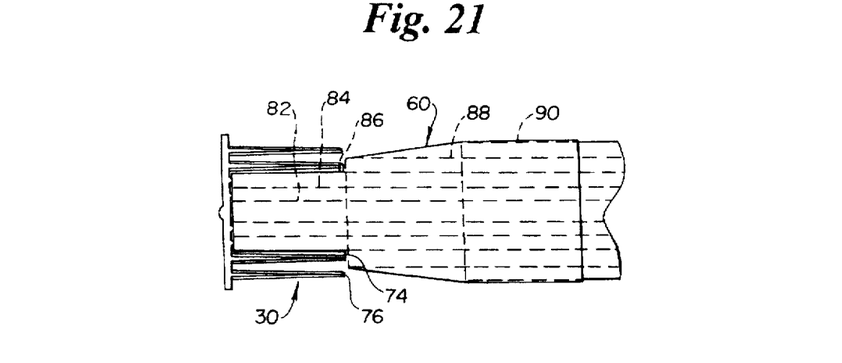
Figure 22:
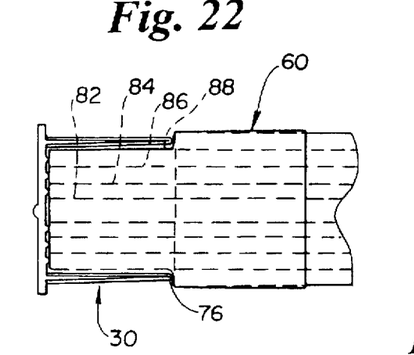
Figure 23:
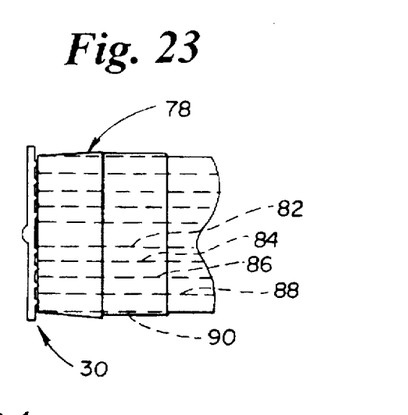

In a preferred embodiment, the filter cone 60 is pleated by an automated pleating machine. The automated pleating machine used to pleat the filter cone 60 uses the inside pleat first method, but a machine could be built to pleat using the outside pleat first method. The pleating machine uses four moving forming sleeves 82, 84, 86, and 88 and one fixed forming sleeve 90. The support element is mounted to a moving fixture which pushes it into the sleeves 100. All the sleeves 100 and the support element 30 are aligned along the same central axis. The first step is to install the support element 30 in its fixture. The second step is to pull the cone 30 over the fixed sleeve 90 with the inner four sleeves 82, 84, 86, and 88 retracted inside the fifth sleeve 90. The inner four sleeves 82, 84, 86, and 88 are then extended into the cone 60 to fill it out (FIG. 18). Next the pleating cycle is initiated and the support element 30 is moved toward the sleeves 100 so as to drive the cone tip down into the first annular member 70 and into the grooves 45 on the surface of the spokes 46 of the support element 30 (FIG. 19). When the first sleeve 82 bottoms out against the spokes 46 on the support element 30, it is pushed backward by the element so that the second sleeve begins to drive the cone 60 into the gap between the to first annular member 70 and second annular member 72 of the support element 30 and into the grooves on the spokes 46. Thus, the second pleat is formed (FIG. 20). The pleating process continues (FIGS. 21 and 22) until all four of the moveable sleeves 82, 84, 86, and 88 have been pushed back inside the fifth sleeve 90, the fifth sleeve 90 has been used to pleat the cone 60 over the outside of the support element 30 and into circular groove 47, and all the pleats have been formed (FIG. 23). The support element 30 then is withdrawn from the sleeves 100 which remain retracted. In a preferred embodiment, the support element 30 is rotated as it is withdrawn from the sleeves 100 so there is less chance of the pleats of the pleated cone 60 becoming snagged on one of the sleeves 100.

3. Ultrasonically Staking the Filter Cone 60 to the Support Element 30

Figure 24:
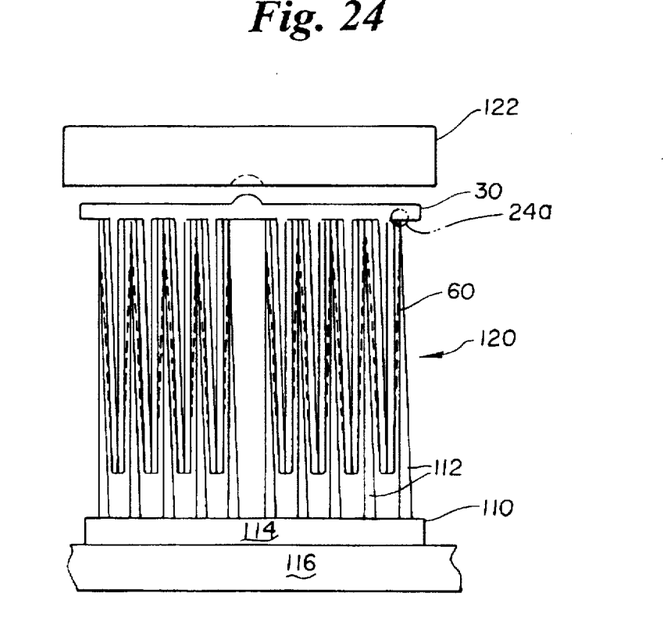
FIG. 24 is a cross-sectional side view of the step of ultrasonically staking the filter cone to the support element.
Figure 24A:
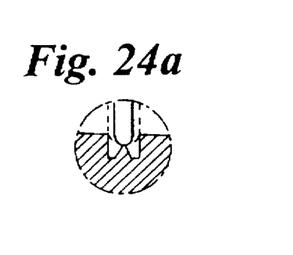

The support element 30 with a cone 60 pleated onto it is placed upside down in a welding nest 110. The welding nest 110 comprises concentric sleeves 112 attached to a base disk 114 which in turn rests on the table 116 of the ultrasonic welding machine 120 (FIG. 24). The concentric sleeves 112 of the welding nest 110 press the cone 60 against the energy directors 118 on the spokes 46 of the support element 30 in the areas between the annular members 70, 72, 74, and 76, and on the base ring 44 outside annular member 76. A detail of an energy director 118 is shown in the circled portion of FIG. 24. When the ultrasonic welding machine 120 is activated, the horn 122 of the welder 120 is lowered until it presses down on the bottom surface of the base of the support element 30 which is not facing upward (FIG. 24). The horn 122 is excited so it vibrates at a specific frequency and amplitude. The horn 122 in turn vibrates the support element 30 which causes the energy directors 118 to be vibrated against the creases in the pleats of the cone 60. A portion of the support element 30 between the moving energy directors 118 and the cone 60 melts and the cone 60 is embedded in the molten plastic. The vibration is then terminated and the horn 122 is held against the base of the element 30 for a time to allow the molten plastic to harden. The bond of the cone 60 to the element 30 is mechanical. The bond of the cone 30 to the base ring 44 is the most important bond because it forms a seal which prevents blood from passing from the blood inlet chamber 34 to the blood outlet chamber 36 of the filter 10 without going through the filter cone 60.

In a preferred embodiment, the melting point of the support element 30 is lower than that of the cone 60 so that only the portions of the support element 30 near the energy directors 118 melt. The filter screen of the cone 60 remains intact and is not significantly damaged or weakened by the heat or vibration. In a preferred embodiment, the support element 30 is made of ABS plastic and the cone 60 is made of polyester. An energy director 118 facilitates the staking, but the cone also could be staked to the bottom or sides of the base ring 44 of the element 30.

The support element 30 may be made of any appropriate material. Any type of medical grade plastic is preferred. The filter screen of the cone 60 also may be made of any appropriate material. Any type of medical grade plastic filter material is preferred. In one preferred embodiment, the filter screen of the cone 60 is woven from polyester monofilament fiber having a nominal diameter of 30.25 microns. The pores in the filter screen have a nominal size of 38 microns and the nominal percentage of open area is 31 percent.

The cone 60 may be bonded to the support element 30 with an adhesive instead of ultrasonic staking, or in addition to ultrasonic staking. Also, the cone 60 could be staked or bonded to the support element 30 in places other than, or in addition to, the spokes 46 and base ring 44 of the base of the support element 30.

4. Trimming the Pleated Cone 60

Figure 25:
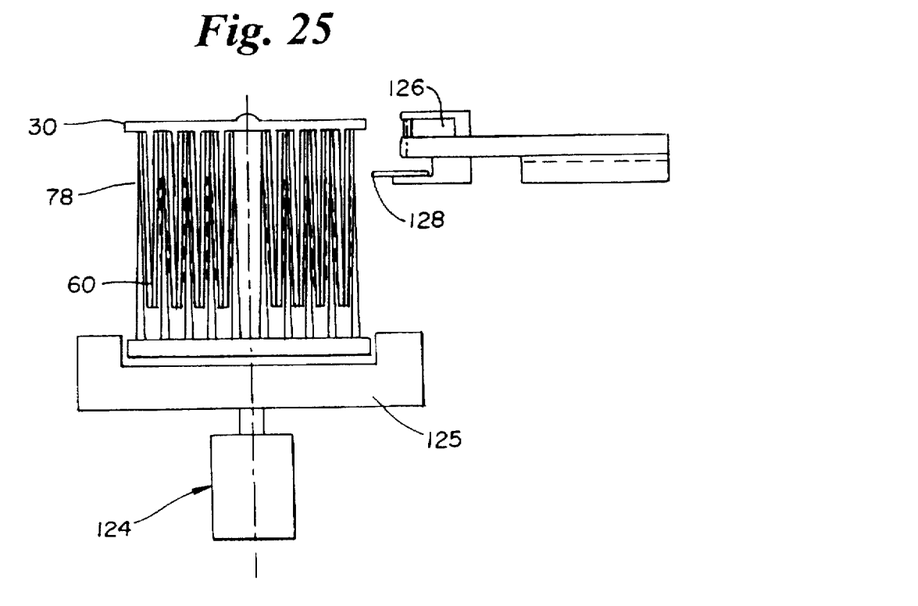
FIG. 25 is a cross-sectional side view of the step of cutting the excess cone material away from the support element.

With the support element 30 still located in the welding nest 110, the welding nest 110 is placed in a fixture 125 to trim off the extra cone material 78 which extends beyond the staking point on the support element 30 and wraps around the outside sleeve of the welding nest 110. The fixture 125 rotates the welding nest 110 and thus the pleated cone 60 while a cutting blade 126 and a depth wheel 128 are pressed against the outside surface of the welding nest 110 to trim off the extra cone material 78 (FIG. 25). The fixture 125 is rotated by a motor 124.

5. Dispensing the UV Activatable Adhesive Into the Base Portion 16

A separate base portion 16 is positioned on a support fixture. A dispensing needle then moves into a precise position in close proximity to the separate base portion 16 and the adhesive is dispensed through the tip of the needle as the separate base portion 16 rotates below it.

6. Placing the Support Element 30 on Top of the Adhesive

An integrated wall portion 14 and cap portion 12 is inserted into a fixture above the separate base portion 16 and the integrated wall portion 14 and cap portion 12 is held in place. A locating arm then moves a guide into position to align the placement of the support element 30 above the separate base portion 16. The element 30 is slid down the guide until it rests in the adhesive.

7. Attaching the Wall Portion 14 to the Base Portion 30

Figure 26:
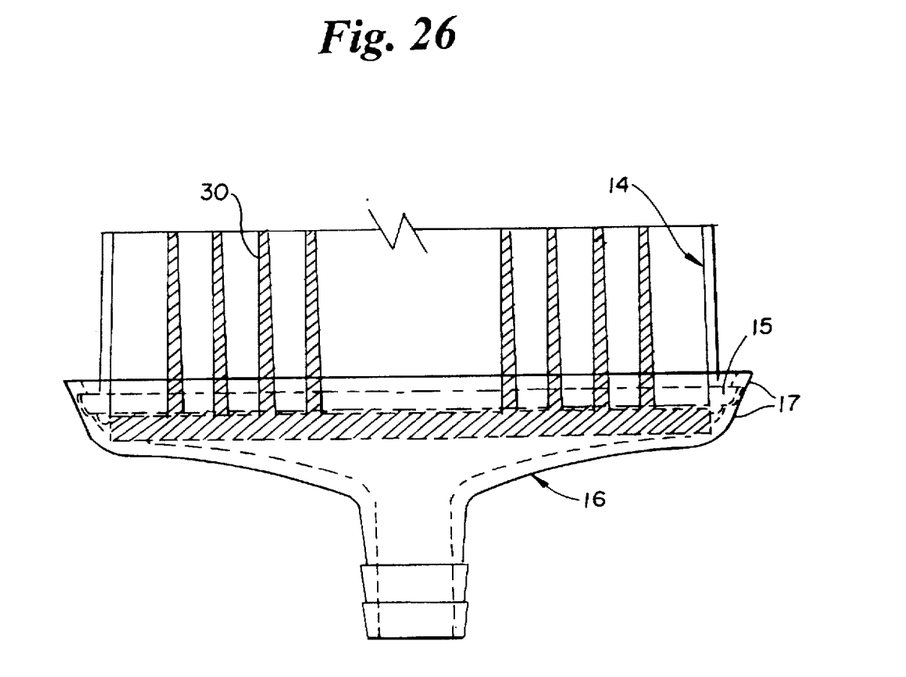
FIG. 26 is a cross-sectional side view of the lower portion of the filter.

The integrated wall portion 14 and cap portion 12 is lowered at a controlled rate onto the separate base portion 16 until the outer lip 15 of the integrated wall portion 14 and cap portion 12 is embedded in the adhesive and captured by the mating components of the snap joint 17 on the separate base portion 16. The support element 30 is pressed into the adhesive and held against the separate base portion 16 by the bottom of the integrated wall portion 14 and cap portion 12. The adhesive seals the gap between the separate base portion 16 and support element 30, and integrated wall portion 14 and cap portion 12 and support element 30. The adhesive also bonds and seals the separate base portion 16 to the integrated wall portion 14 and cap portion 12. Thus, a triple joint is formed (FIG. 26). The assembled filter 10 can now be moved to the next station.

8. Curing the UV Activatable Adhesive

The assembled filter 10 is placed on a support fixture. The support fixture lowers the filter 10 into a chamber and a cover door slides over the top of the chamber. A UV emitting bulb is turned on (or exposed by shutters) for a fixed interval to cure the adhesive in the filter 10. The cover door retracts when the light is turned off (or shuttered) and the filter 10 is raised out of the chamber and removed by the operator. The manufacturing process is now complete.

From the foregoing detailed description of specific embodiments of the invention, it is apparent that an improved blood filter and an improved method of manufacturing a fluid filter have been disclosed. Although particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims.

What is claimed is:

1. A method of manufacturing a fluid filter comprising:
   (a) providing a cone having a tip end and an open end and made of a filter material;
   (b) providing a support element having a plurality of concentric annular members mounted on a base and having outermost and innermost concentric annular members;
   (c) aligning the central axes of the cone and the support element with the tip end of the cone closest to the support element; and
   (d) inserting a portion of the cone into a circular area between two concentric annular members by placing a forming sleeve inside the cone and inserting the forming sleeve between the two concentric annular members, the concentric annular members being generally cylindrical and having an interior and an exterior.

2. The method of claim 1, wherein the forming sleeve is an annular forming sleeve.

3. The method of claim 1, wherein a second portion of the cone is inserted into the interior of the innermost annular member by a forming sleeve.

4. The method of claim 3, wherein the portion of the cone that is inserted in the interior of the innermost annular member is attached to the base of the support element.

5. The method of claim 1, wherein a second portion of the cone is formed over the exterior of the outermost annular member by a forming sleeve inserted outside the outermost annular member.

6. The method of claim 1, wherein a second portion of the cone is inserted into the interior of the innermost annular member and a third portion of the cone is formed over the exterior of the outermost annular member by inserting a forming sleeve outside the outermost annular member.

7. The method of claim 6, wherein each portion of the cone which is inserted into the support element is inserted substantially to the base of the support element.

8. The method of claim 7, wherein each portion of the cone which is inserted into the support element is inserted to the base of the support element.

9. The method of claim 1, wherein the portion of the cone inserted into the area between the two concentric annular members is inserted substantially to the base of the support element.

10. The method of claim 1, wherein each of a plurality of portions of the cone is inserted into separate circular areas between two concentric annular members by a plurality of forming sleeves.

11. The method of claim 10, wherein the plurality of forming sleeves are inserted into the separate circular areas by an automated machine.

12. The method of claim 9, wherein a first additional portion of the cone is inserted into the interior of the innermost annular member by a forming sleeve and a second additional portion of the cone is formed over the exterior of the outermost annular member by a forming sleeve inserted outside the outermost annular member.

13. The method of claim 12, wherein the first additional portion of the cone which is inserted into the circular area in the interior of the innermost annular member is the first portion of the cone to be inserted into the support element, each of the plurality of portions of the cone inserted into the circular areas between the two concentric annular members are inserted in order from the innermost to outermost circular areas, and the second additional portion of the cone is formed over the exterior of the outermost annular member after all of the other pleats have been formed.

14. The method of claim 12, wherein each portion of the cone which is inserted into the support element is inserted substantially to the base of the support element.

15. The method of claim 14, wherein each portion of the cone that is inserted into the support element is inserted to the base of the support element.

16. The method of claim 15, wherein each portion of the cone that is inserted into the support element is attached to the base of the support element.

17. The method of claim 16, wherein each portion of the cone that is inserted into the support element is attached to the base of the support element by inserting a portion of the cone into a groove on the base of the support element, and then subjecting the base of the support element to ultrasonic vibrations.

18. The method of claim 12, wherein each of the forming sleeves is inserted by an automated machine.

19. The method of claim 12, wherein each of the forming sleeves is part of an automated machine comprising a base and the forming sleeves, wherein the forming sleeves are retractable, and wherein the base has a face from which the forming sleeves can be extended.

20. The method of claim 19, wherein the open end of the cone is placed partially over the face of the base from which the forming sleeves can be extended with the forming sleeves retracted and then the forming sleeves are extended.

21. The method of claim 20, wherein the support element is fixed and the cone and the extended forming sleeves are moved toward the support element and each forming sleeve is brought into contact in succession with the support element until the cone is pleated.

22. The method of claim 21, wherein the first additional portion of the cone which is inserted into the circular area in the interior of the innermost annular member is the first portion of the cone to be inserted into the support element, each of the plurality of portions of the cone inserted into the circular areas between the two concentric annular members are inserted in order from the innermost to outermost circular areas, and the second additional portion of the cone is formed over the exterior of the outermost annular member after all of the other pleats have been formed.

23. The method of claim 20, wherein the support element is moved toward the cone after the sleeves are extended and the support element is brought in contact with each forming sleeve in succession until the cone is pleated.

24. The method of claim 23, wherein the first additional portion of the cone which is inserted into the circular area in the interior of the innermost annular member is the first portion of the cone to be inserted into the support element, each of the plurality of portions of the cone inserted into the circular areas between the two concentric annular members are inserted in order from the innermost to outermost circular areas, and the second additional portion of the cone is formed over the exterior of the outermost annular member after all of the other pleats have been formed.

25. The method of claim 23, wherein each portion of the cone that is inserted into the support element is attached to the base of the support element.

26. The method of claim 25, wherein each portion of the cone that is attached to the base of the support element is attached by ultrasonic vibrations.

27. The method of claim 1, wherein the portion of the cone that is inserted between the two concentric annular members is attached to the base of the support element.

28. The method of claim 27, wherein the portion of the cone that is inserted between the two concentric annular members is attached to the base of the support element by an additional support element disposed immediately over the filter material.

29. The method of claim 27, wherein the portion of the cone that is inserted into the circular area is attached to the base of the support element by ultrasonic vibrations.

30. The method of claim 27, wherein the portion of the cone that is inserted into the circular area is attached to the base of the support element by inserting a portion of the cone into a groove on the base of the support element.

31. The method of claim 27, wherein the portion of the cone that is inserted into the circular area is attached to the base of the support element by inserting a portion of the cone into a groove on the base of the support element, and then subjecting the base of the support element to ultrasonic vibrations.

32. The method of claim 31, wherein the ultrasonic vibrations are conducted through energy directors.

33. The method of claim 31, wherein the support element has a lower melting temperature than the cone.

34. The method of claim 27, wherein the portion of the cone that is inserted into the circular area is attached to the base of the support element by an adhesive.

35. The method of claim 1, wherein a second portion of the cone is attached to a portion of the base of the support element which is outside the outermost concentric annular member.

36. The method of claim 35, wherein the second portion of the cone that is attached to the portion of the base of the support element is attached by ultrasonic vibrations.

37. The method of claim 35, wherein the second portion of the cone that is attached to the portion of the base of the support element is attached by inserting a portion of the cone into a groove on the base of the support element.

38. The method of claim 35, wherein the second portion of the cone that is attached to the portion of the base of the support element is attached by an adhesive.

39. The method of claim 35, wherein the second portion of the cone that is attached to the portion of the base of the support element is attached by an additional support element disposed immediately over the filter material.

40. The method of claim 35, wherein the second portion of the cone that is attached to the portion of the base of the support element is attached by inserting a portion of the cone into a groove on the base of the support element, and then subjecting the base of the support element to ultrasonic vibrations.

41. The method of claim 40, wherein the ultrasonic vibrations are conducted through energy directors.

42. The method of claim 40, wherein the support element has a lower melting temperature than the cone.

43. The method of claim 1, wherein the support element has a lower melting temperature than the cone.

44. The method of claim 1, wherein the base of the support element is cylindrical.

45. The method of claim 1, wherein the support element has from two to six concentric annular members.

46. The method of claim 1, wherein the support element has from two to four concentric annular members.

47. The method of claim 1, wherein the support element has four concentric annular members.

48. The method of claim 1, wherein the fluid filter is a blood filter.

49. The method of claim 1, wherein the forming sleeve is inserted.

50. The method of claim 1, further comprising:
   (a) providing an unassembled housing having an integrated cap portion and a generally cylindrical wall portion and a separate base portion;
   (b) dispensing adhesive into the separate base portion;
   (c) inserting the support element containing a portion of the cone into the separate base portion and into the adhesive; and
   (d) attaching the integrated cap portion and generally cylindrical wall portion to the separate base portion.

51. The method of claim 50, wherein the fluid filter is a blood filter, the integrated cap portion and a generally cylindrical wall portion comprises a blood inlet and a gas vent, and the separate base portion comprises a blood outlet.

52. The method of claim 50, wherein the adhesive is cured by ultraviolet radiation.

53. A method of manufacturing a fluid filter comprising:
   (a) providing a cone having a tip end and an open end and made of a filter material;
   (b) providing a support element having a plurality of concentric annular members mounted on a base and having outermost and innermost concentric annular members;
   (c) aligning the central axes of the cone and the support element with the open end of the cone closest to the support element; and
   (d) inserting a portion of the cone into a circular area between two concentric annular members by placing a forming sleeve over the cone and inserting the forming sleeve between the two concentric annular members, the concentric annular members being generally cylindrical and having an interior and an exterior.

* * * * *